United States Patent [19]

Kohno et al.

[11] Patent Number: 5,373,850
[45] Date of Patent: Dec. 20, 1994

[54] FLOW-VELOCITY SENSOR PROBE

[75] Inventors: Hiromasa Kohno; Kouji Tsuchida; Yoshio Ishitsu; Masaru Kurio; Shigekazu Sekii, all of Nakai, Japan

[73] Assignee: Terumo Kabushiki Kaisha, Tokyo, Japan

[21] Appl. No.: 888,464

[22] Filed: May 21, 1992

Related U.S. Application Data

[63] Continuation of Ser. No. 644,616, Jan. 23, 1991, abandoned.

[30] Foreign Application Priority Data

Jan. 29, 1990 [JP] Japan ................... 2-16098

[51] Int. Cl.$^5$ .................................... A61B 5/00
[52] U.S. Cl. ..................... 128/692; 128/713; 128/736
[58] Field of Search ............ 128/713, 736, 691–693; 73/204.22, 204.25

[56] References Cited

U.S. PATENT DOCUMENTS

| | | | |
|---|---|---|---|
| 3,075,515 | 1/1963 | Richards | 128/692 |
| 3,438,253 | 11/1966 | Kuether et al. | |
| 3,595,079 | 7/1971 | Grahn | |
| 3,678,922 | 7/1972 | Phillips et al. | |
| 3,789,831 | 2/1974 | Kopaniky et al. | |
| 3,820,530 | 6/1974 | Gilford et al. | |
| 3,995,623 | 12/1976 | Blake | |
| 4,004,576 | 1/1977 | Gahwiler et al. | |
| 4,035,622 | 7/1977 | Obermajer | |
| 4,230,126 | 10/1980 | Elings | |
| 4,240,441 | 12/1980 | Khalil | |
| 4,354,504 | 10/1982 | Bro | 128/691 |
| 4,380,237 | 4/1983 | Newbower | |
| 4,502,488 | 3/1985 | Degironimo et al. | |
| 4,542,748 | 9/1985 | Roy | |
| 4,548,516 | 10/1985 | Helenowski | 128/691 |
| 4,572,206 | 2/1986 | Geddes et al. | |
| 4,595,015 | 6/1986 | Jansen et al. | |
| 4,621,646 | 11/1986 | Bryant | |
| 4,628,743 | 12/1986 | Miller, Jr. et al. | 73/204.25 |
| 4,632,125 | 12/1986 | Webler et al. | |
| 4,685,470 | 8/1987 | Sekii et al. | |
| 4,841,981 | 6/1989 | Tanabe et al. | |
| 4,901,734 | 2/1990 | Griffin et al. | |
| 4,960,109 | 10/1990 | Lele | 128/736 |

OTHER PUBLICATIONS

Medical and Biological Engineering, vol. 11, No. 2, Mar. 1973, pp. 201–205, Stevenage, Herts, GB; A. L. Delaunois: "Thermal method for continuous blood–velocity measurements in large blood vessels, and cardiac-output determination".

*Primary Examiner*—Lee S. Cohen
*Assistant Examiner*—Robert L. Nasser, Jr.
*Attorney, Agent, or Firm*—Frishauf, Holtz, Goodman & Woodward

[57] ABSTRACT

A flow-velocity sensor probe includes a thermistor for generating heat which is placed in a fluid, and a waterproof resin and a metal piece for easily radiating the heat generated by the thermistor. The flow velocity of the fluid is measured continuously from a change of temperature in the thermistor, and the thermistor is provided in close proximity to the metal piece for transmitting the heat to the fluid.

8 Claims, 4 Drawing Sheets

| PROBE TYPE | HIGH FLOW-RATE REGION | | LOW FLOW-RATE REGION | | NUMBER OF PROBES MEASURED |
|---|---|---|---|---|---|
| | A VALUE | B PARAMETER | A VALUE | B PARAMETER | |
| PROBE OF THIS INVENTION | 9.506 | 56.866 | 13.537 | 57.477 | 2 |
| PRIOR-ART PROBE | 1.250 | 59.761 | 2.532 | 59.967 | 3 |

FLOW-VELOCITY SENSOR PROBE

This application is a continuation of application Ser. No. 07/644.616, filed Jan. 23, 1991, now abandoned.

BACKGROUND OF THE INVENTION

This invention relates to a flow-velocity sensor probe used in flow-velocity measurement such as measurement of cardiac output.

In measurement of cardiac output which is essential in managing critically ill patients with cardiac failure, conventionally use is made of methods that rely upon ultrasound, dye dilution and radioisotopes, etc. Owing to its simplicity and accuracy, wide use is made of a thermodilution method based upon the right-heart catheter method, in which a catheter is held in the pulmonary artery.

However, the information obtained in the thermodilution method is discontinuous. In addition, when cardiac output is measured, an infusion fluid must be injected each time a measurement is taken. Owing to such problems as the complexity of surgery, infection which accompanies the repeated injection of a cold saline solution, a drop in body temperature and increased load on the heart, the number of times measurements can be taken is limited, especially in case of a seriously ill patient whose cardiac output needs to be ascertained.

One method of continuously measuring cardiac output very precisely is a method using the CCOM system (continuous cardiac output monitoring system) developed by the present inventors (U.S. Pat. No. 4,685,470). This monitoring system includes a catheter probe and a monitoring unit. By continuously measuring the amount of heat loss, which is due to blood flow, using a thermistor (referred to as a CFT) self-heated by passage of a current therethrough, cardiac output is monitored continuously without the intermittent injection of a cold saline solution.

Cardiac output (CO) is the amount of blood expelled from the heart in a unit of time and usually is expressed by a value per minute. Ordinarily, if the heart or a major blood vessel is not short-circuited, the amount of blood expelled from the right heart and that expelled from the left heart are equal, and cardiac output CO (L/min) is obtained in accordance with the following equation from flow velocity (cm/sec) in the pulmonary artery and the cross-sectional area s (cm²) of the pulmonary artery:

$$CO = 0.06 \cdot s \cdot v \quad (1)$$

The principle of continuous measurement of cardiac output will now be described.

A thermistor is used as an ordinary temperature sensor and operates on the basis of a change in resistance value in dependence upon a change in temperature.

Since a thermistor is also a resistor, the thermistor itself emits heat when a large amount of current is passed through it. Accordingly, when such a thermistor is placed in the bloodstream, the temperature of the thermistor becomes that at which equilibrium is established between the amount of heat produced by the electric current and the amount of heat carried away by the flow of blood. Since this equilibrium temperature Tt varies in dependence upon the flow velocity, the thermistor can be utilized as a flow-velocity sensor.

The relationship between equilibrium temperature Tt (C°) and blood flow velocity (cm/sec) can be expressed by the following equation, which is based upon experimentation:

$$\log Tt = A \cdot \log v + B \quad (2)$$

where A and B are constants dependent upon the fluid and the characteristics of the thermistor, etc.

In order to measure cardiac output CO continuously, it is necessary to obtain a relation between the equilibrium temperature Tt and CO. Therefore, cancelling the flow velocity v from Eqs. (1) and (2) gives us the following equation:

$$\log Tt = A \cdot \log CO + B - A \cdot \log (0.06 \cdot s) \quad (3)$$

However, Eq. (3) includes an unknown parameter, namely the cross-sectional area s of the pulmonary artery, and cannot be used as is in measuring cardiac output. Accordingly, if cardiac output and equilibrium temperature are measured at least once and the measured values are substituted into Eq. (3) as calibration values $CO_{CAL}$ and $Tt_{CAL}$, we have $$\log Tt_{CAL} = A \cdot \log CO_{CAL} + B - A \cdot \log (0.06 \cdot s) \quad (4)$$

When the cross-sectional area s of the pulmonary artery is cancelled from Eqs. (3) and (4), we obtain $$\log (Tt/Tt_{CAL}) = A \cdot \log (CO/CO_{CAL}) \quad (5)$$

Accordingly, cardiac output CO can be expressed by the following equation as a function of equilibrium temperature Tt:

$$CO = CO_{CAL} \cdot (Tt/Tt_{CAL})^{1/A} \quad (6)$$

This makes it possible to measure cardiac output continuously using a self-heating thermistor.

A method of calculating cardiac output using the CCOM system will now be described.

In a CCOM system, the above-mentioned calibration is performed by the thermodilution method, and two thermistors are attached to a catheter probe. One of these thermistors is a self-heating CFT thermistor for measuring equilibrium temperature and a PAT thermistor for measuring blood temperature using the thermodilution method.

CFT thermistor temperature $Tt_R$ is dependent upon a change in blood flow velocity but is also dependent upon a change in blood temperature TB. Accordingly, a correction in $Tt_R$ which accompanies a change in blood temperature from the time of calibration is carried out in accordance with the following equation:

$$Tt = Tt_R - K \cdot (TB - TB_{CAL}) \quad (7)$$

where
$Tt_R$: CFT thermister temperature at time of measurement
K: blood temperature correction coefficient
TB: blood temperature
$TB_{CAL}$: blood temperature at time of calibration If the temperature correction of Eq. (7) is applied to Eq. (6), the following equation is obtained:

$$CO = CO_{CAL} \cdot \{[Tt_R - K \cdot (TB - TB_{CAL})]/Tt_{CAL}\}^{1/A} \quad (8)$$

Thus, as set forth above, cardiac output CO can be calculated in accordance with Eq. (8) from the continuously measured CFT-thermistor temperature $Tt_R$ and blood temperature TB. However, when the full range (0–12 L/min) of cardiac output is calculated with the value of the constant A in Eq. (8) being a simple value, there is a decline in precision. Therefore, the range over which cardiac output is measured is divided into two parts. Specifically, cardiac output is calculated using arithmetic expressions for a case where the value of A when the cardiac output is in a high flow-rate region is AH and a case where the value of A when the cardiac output is in a low flow-rate region is AL. It should be noted that the constant A is an index of temperature with regard to flow velocity and shall be referred to as the "A value" hereinafter.

(1) Processing in a case where the calibration value $CO_{CAL}$ of cardiac output is greater than 2.75 L/min:

Initially, calibration of cardiac output is carried out by the thermal dilution method. Next, the CFT-thermistor temperature $Tt_{2.75}$ when the cardiac output is 2.75 L/min is calculated from the calibration values ($CO_{CAL}$ and $Tt_{CAL}$). That is, when Eq. (6) is transformed into an equation which obtains Tt and CO=2.75 L/min is substituted into the equation with the A value serving as AH, we have $$Tt_{2.75} = Tt_{CAL} \cdot (2.75/CO_{CAL})^{AH} \qquad (9)$$

At the time of measurement, cardiac output is obtained in accordance with the following arithmetic expressions where the measurement range is divided into two parts:

① When $Tt_R - K \cdot (TB - TB_{CAL}) > Tt_{2.75}$ $$CO = 2.75 \times \left[ \frac{Tt_R - K \cdot (TB - TB_{CAL})}{Tt_{2.75}} \right]^{1/AL} \qquad (10)$$

② When $Tt_R - K \cdot (TB - TB_{CAL}) \leq Tt_{2.75}$ $$CO = CO_{CAL} \times \left[ \frac{Tt_R - K \cdot (TB - TB_{CAL})}{Tt_{CAL}} \right]^{1/AH} \qquad (11)$$

(2) Processing in a case where the calibration value $CO_{CAL}$ of cardiac output is less than 2.75 L/min:

As in the case of (1) above, the CFT-thermistor temperature $Tt_{2.75}$ when the cardiac output is 2.75 L/min is calculated from the calibration values ($CO_{CAL}$ and $Tt_{CAL}$). That is, the A value is adopted as AL as the following is obtained from Eq. (6):

$$Tt_{2.75} = Tt_{CAL} \cdot (2.75/CO_{CAL})^{AL} \qquad (12)$$

At the time of measurement, cardiac output is obtained in accordance with the following arithmetic expressions where the measurement range is divided into two parts:

① When $Tt_R - K \cdot (TB - TB_{CAL}) > Tt_{2.75}$ $$CO = CO_{CAL} \times \left[ \frac{Tt_R - K \cdot (TB - TB_{CAL})}{Tt_{CAL}} \right]^{1/AL} \qquad (13)$$

② When $Tt_R - K \cdot (TB - TB_{CAL}) \leq Tt_{2.75}$ $$CO = 2.75 \times \left[ \frac{Tt_R - K \cdot (TB - TB_{CAL})}{Tt_{2.75}} \right]^{1/AH} \qquad (14)$$

FIG. 1 illustrates the structure of a conventional flow-velocity sensor probe (catheter probe). The probe includes a catheter tube 1 and a balloon inflating line 9, a pressure measuring line 10, an infusion fluid injecting line 11 and a thermistor connecting line 12, all of which are connected to the catheter tube 1 via a manifold 6.

The structure of the catheter tube 1 is such that a pressure measuring aperture 4, a CFT thermistor 2 and a PAT thermistor 3 are disposed at the tip of the catheter tube. The CFT thermistor 2 and PAT thermistor 3 are electrically connected to a CFT connector 7 and a PAT connector 8, respectively.

FIG. 2 illustrates the structure of the CFT thermistor mount in the conventional flow-velocity sensor probe.

As shown in FIG. 2, the CFT thermistor 2 is dipped in a waterproof epoxy resin 34 in order to assure a waterproof condition and is then inserted into a tube 31 made of polyimide. The CFT thermistor 2 inserted into the tube 31 is fitted into a side aperture 29 in the catheter tube 1, and the thermistor 2 is then bonded into place by an epoxy bonding agent 36 in order to fix the thermistor to the catheter tube 1.

Thermistor leads 32 are passed through the interior of the catheter tube 1 and are electrically connected to the CFT connector 7 of the thermistor connecting line 12.

A number of problems are encountered in the prior art. Specifically, in the conventional CCOM system described above, the change in the temperature of the CFT thermistor regarding blood flow is small and the sensitivity needed in order to measure cardiac output is unsatisfactory. More specifically, in the CFT thermistor mount of the flow-velocity sensor probe (catheter probe), the structure is such that a resin having poor thermal conductivity located between the CFT thermistor and the outside (blood) blocks the efficient transfer of heat, which is emitted by the CFT thermistor, to the outside, and therefore cooling by the blood cannot be carried out sufficiently.

In addition, the conventional flow-velocity probe (catheter probe) allows escape of heat along the thermistor leads, and this has an affect upon the temperature of the PAT thermistor.

SUMMARY OF THE INVENTION

Accordingly, an object of the present invention is to provide a flow-velocity sensor probe which solves the aforementioned problems encountered in the prior art.

According to the present invention, the foregoing object is attained by providing a flow-velocity sensor probe comprising heat generating means placed in a fluid, temperature detecting means for detecting temperature produced by the heat generating means, and thermally conductive heat radiating means for radiating heat, which is generated by the heat generating means, by transmitting the heat to the fluid, the thermally conductive heat radiating means being provided in close proximity to the heat generating means.

In such an arrangement, a change in the temperature of the CFT thermistor with respect to blood is enlarged to raise the sensitivity of flow velocity measurement.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

A preferred embodiment of the present invention will now be described in detail with reference to the accompanying drawings.

Figure 1:
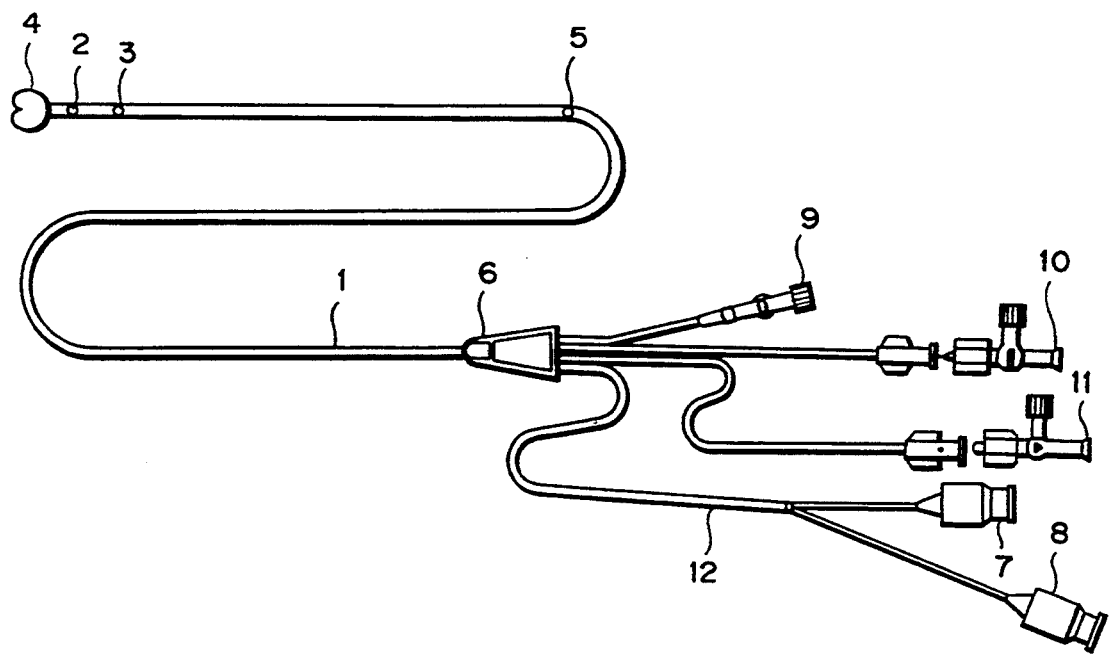
FIG. 1 is a diagram showing the structure of a flow-velocity sensor probe (catheter probe) according to the prior art.
Figure 2:
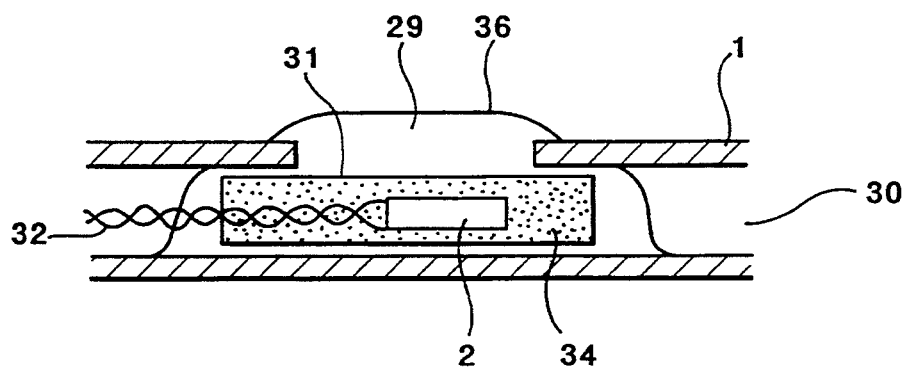
FIG. 2 is a diagram showing the structure of a CFT thermistor mounting portion in the flow-velocity sensor probe according to the prior art.
Figure 3:
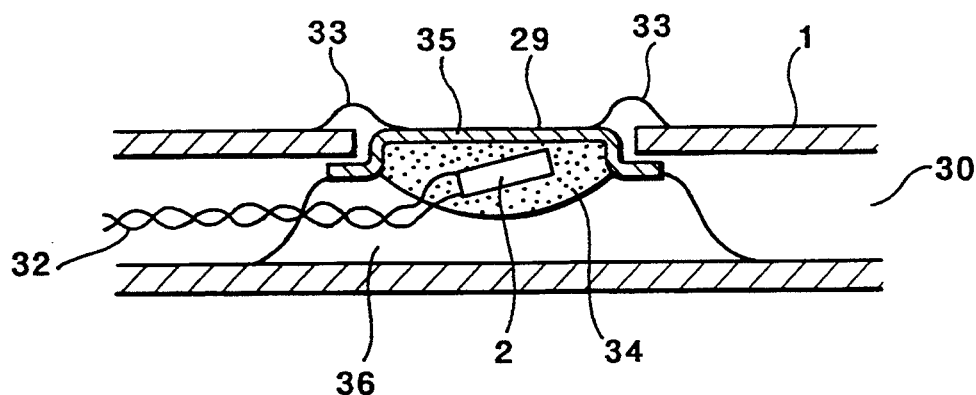
FIG. 3 is a diagram showing a flow-velocity sensor probe according to an embodiment of the present invention and illustrating the structure of a CFT thermistor mounting portion in the side aperture of a catheter.

FIG. 3 is a diagram showing a flow-velocity sensor probe according to an embodiment of the present invention and illustrating the structure of a CFT thermistor mounting portion in the side aperture of a catheter.

As illustrated in FIG. 3, the CFT thermistor 2 is dipped in the waterproof epoxy resin 34 in order to assure a waterproof condition and is then bonded to a small metal piece 35. Resin 34 also is an electrical insulator. The small metal piece 35 consists of gold (Au), which has a high thermal conductivity. Boron nitride (BN), having a high thermal conductivity, is mixed with the waterproof epoxy resin 34 for the purpose of enhancing its thermal conductivity. Silicon nitride, alumina and diamond may be used for the purpose of enhancing the thermal conductivity of the epoxy resin 34.

The CFT thermistor 2 affixed to the small metal piece 35 is bonded into place by the epoxy bonding agent 36 in order to fix the thermistor in the side aperture 29 to the catheter tube 1. In order to maintain a waterproof seal between the side aperture 29 of the catheter and the small metal piece 35, the thermistor and the catheter tube (made of vinyl chloride) are bonded by an epoxy bonding agent 33, which exhibits an excellent adhesive property. A material having excellent thermal conductivity is selected and used as the waterproof epoxy resin 34.

The thermistor leads 32 are electrically connected to the CFT connector 7 of the thermistor connecting line 12 through the interior of the catheter probe 1. Passing an electric current via the thermistor leads 32 causes the thermistor 2 to produce heat, which is transmitted to the outside via the resin 34 and the metal piece 35.

The sensitivity of the flow-velocity sensor probe to flow velocity can be expressed using the abovementioned A value as an index.

Figure 4:
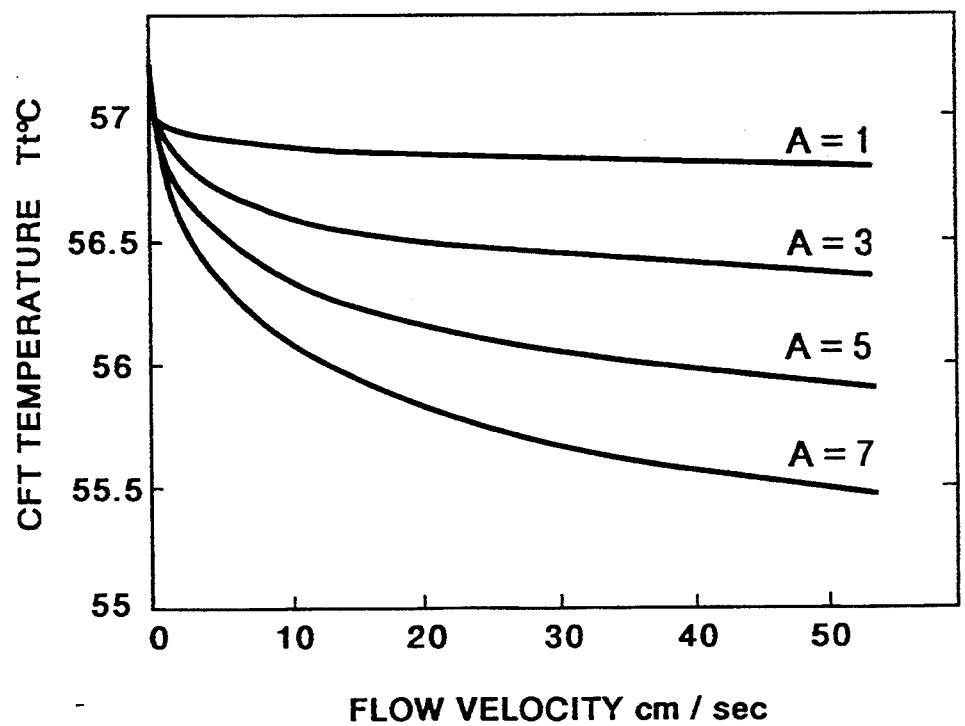
FIG. 4 is a diagram showing the relationship between A values and a change in the temperature of a CFT thermistor plotted against calculated flow velocity.

FIG. 4 illustrates the relationship between the A value and a change in CFT thermistor temperature plotted against flow velocity calculated from Eq. (2).

As apparent from FIG. 4, the CFT temperature decreases, and therefore the sensitivity of the flow-velocity probe is improved, with an increase in the A value. It should be noted that the A values shown in FIG. 4 are values obtained by multiplying the A in Eq. (2) by -1000.

A system for measuring the A value of the flow-velocity sensor probe will now be described.

Figures 5, 6:
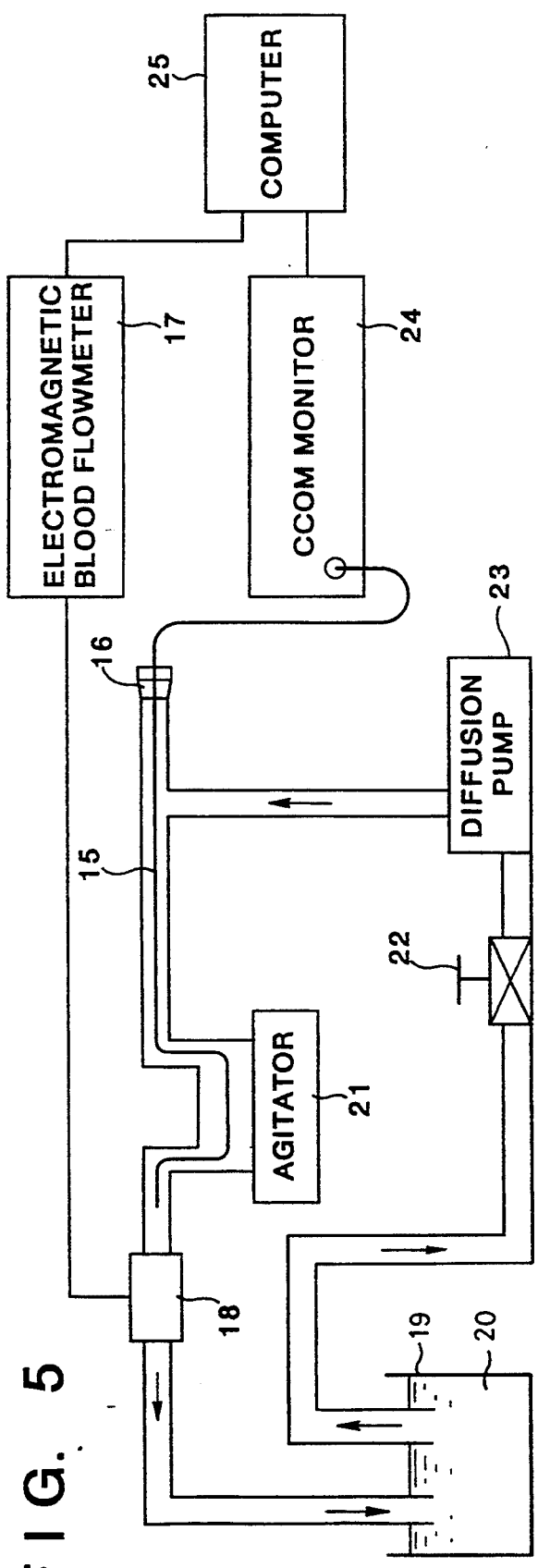
FIG. 5 is a block diagram showing a system for measuring the A value of a flow-velocity sensor probe.
FIG. 6 is a diagram showing a comparison between the performance of a flow-velocity sensor probe according to the present invention and the performance of a conventional probe.

FIG. 5 is a block diagram showing a system for measuring the A value of the flow-velocity sensor probe. The system is constituted by a acrylic tube having a diameter of 20 mm and a tube made of vinyl chloride. A saline solution 20 is circulated through this tubing instead of blood. The arrows in FIG. 5 indicate the direction in which the saline solution 20 circulates.

The saline solution 20 is heated to a temperature of 37° C. in an isothermal bath 19, and the solution is regulated to a predetermined flow rate by a diffusion pump 23 and a flow-rate regulating valve 22. The circulating flow rate is measured continuously by an electromagnetic blood flowmeter 17. The value measured by the electromagnetic blood flowmeter 17 is calibrated in advance by being compared with a value obtained using a method of measuring flow rate with a graduated measuring cylinder.

A CCOM catheter probe 15, which is a flow-velocity sensor probe, is inserted via a check valve 16 provided in a circulating circuit 14 and is so arranged that a CFT thermistor is situated downstream of an agitator 21. The agitator 21 agitates the cold saline solution when calibration in the thermal dilution method is carried out, and serves as a substitute for the heart in a living body.

The CFT thermistor is monitored by a CCOM monitor 24, and the electromagnetic blood flowmeter 17 and CCOM monitor 24 are connected to a computer 25.

As for the calculation of the A value, the flow-rate regulating valve 22 is manipulated to reduce the circulating flow rate of the circulating circuit 14 stepwise from 12 L/min. The CFT temperature and PAT temperature (blood temperature) are then measured upon each stepwise reduction in flow rate, and the A value is found from a correlation between these temperatures and the flow velocity calculated from the flow rate indicated by the electromagnetic blood flowmeter 17.

FIG. 6 shows the results of measuring and comparing the performance of the flow-velocity sensor probe of the present invention and the performance of the conventional probe.

In terms of the A value which indicates the sensitivity of a probe in measuring flow velocity, the flow-velocity sensor of the present invention has an A value greater than five times that of the conventional flow-velocity sensor probe in both the high and low flow-rate regions. Furthermore, with regard also to the B parameter [the same as the constant B in Eq. (2)], which is an index illustrating the degree of heat radiation from a probe], that of the probe according to the present invention is lower by about three points. The number of probes was that used in measurement, and the A values and values of the B parameters were average values for the number of probes used in measurement.

Figure 7:
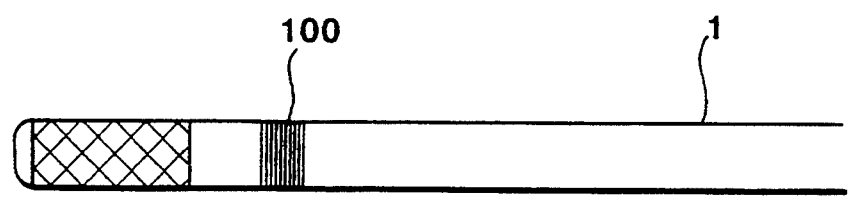
FIG. 7 is a diagram illustrating another embodiment and showing the flow-velocity sensor of the invention fitted into a catheter.
Figure 8:
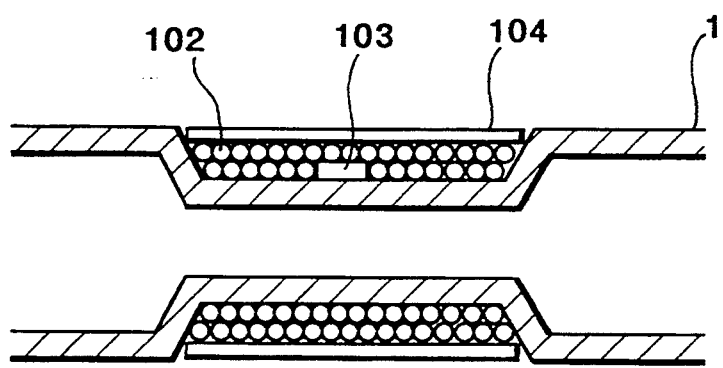
FIG. 8 is an enlarged view showing the structure of this flow-velocity sensor.

FIG. 7 is a diagram illustrating another embodiment and showing the flow-velocity sensor of the invention fitted into a catheter, and FIG. 8 is an enlarged view showing the structure of this flow-velocity sensor.

As shown in FIG. 7, a flow-velocity sensor 100 according to this embodiment is fitted into a catheter tube 1.

In FIG. 8, a nichrome wire 102 is used as the heat generating means in this embodiment and is wound upon the catheter tube 1 from several tens of times to several hundred times. A thermistor 103 for detecting temperature is disposed so as to contact the nichrome wire 102 as much as possible and to be surrounded by the nichrome wire 102. The outer side of the nichrome wire 102 wound upon the catheter tube 1 is covered by a metal ring 104, and the nichrome wire 102 and metal ring 104 used as a means of radiating thermally conductive heat, are contacted and fixed by a waterproof bonding agent. In order that the tube surface of the catheter tube 1 and the outer surface of the metal ring will be flush, the outer diameter of the catheter tube is reduced beforehand by the thickness of the nichrome wire and metal ring.

The nichrome wire used here has a diameter of 0.05 mm and a resistance value of 560.7Ω/m. The wire is sheathed in polyurethane in order to insulate it electrically.

Passing an electric current through the nichrome wire causes the wire to produce heat, which is transmitted to the outside via the metal ring. The extent of transmission depends upon the flow velocity of the exterior fluid. The flow velocity can be measured by measuring the temperature of the nichrome wire at such time.

In accordance with the foregoing embodiments, as described above, heat generated by the CFT thermistor is transmitted to the outside efficiently, and the amount of heat lost along the thermistor leads is reduced. As a result, the sensitivity with which the flow-velocity sensor probe measures flow velocity can be improved.

In addition, since the ratio of the A value in the region of high flow rate to that in the region of low flow rate is reduced, the relation between the CFT temperature and the flow velocity can be calculated very accurately using Eq. (2).

Thus, in accordance with the present invention as described above, heat generated by the CFT thermistor is transmitted to the outside efficiently, and the sensitivity of flow-velocity measurement can be improved.

As many apparently widely different embodiments of the present invention can be made without departing from the spirit and scope thereof, it is to be understood that the invention is not limited to the specific embodiments thereof except as defined in the appended claims.

What is claimed is:

1. A flow-velocity sensor probe which also serves as a heater for a fluid, comprising:

a probe body;

heat generating means, mounted in said probe body, for generating heat when said probe body is placed in a fluid;

detection means, mounted in said probe body, for detecting a temperature of said heat generating means;

a resin layer surrounding both said heat generating means and said detection means, said resin layer including a resin and means for increasing the thermal conductivity of said resin such that said resin layer has a high thermal conductivity and a high electrical resistivity;

thermally conductive heat radiating means, fixed to an outer surface of said probe body so as to contact directly the fluid when the probe body is placed in the fluid, said thermally conductive heat radiating means being substantially flat at the portion thereof which directly contacts the fluid when the probe body is placed in the fluid, said thermally conductive heat radiating means being coupled to an outer portion of said heat generating means which faces the fluid with at least a portion of said resin layer interposed between said outer portion of said heat generating means and said thermally conductive heat radiating means, for radiating heat which is generated by said heat generating means by transmitting the heat to the fluid via said interposed resin layer portion;

surrounding means for partially surrounding said resin layer in said probe body, said surrounding means being made of a substance having a thermal conductivity which is lower than said high thermal conductivity of said resin layer, said surrounding means not surrounding said resin layer at a portion which is facing toward the fluid;

wherein when said probe body is placed in the fluid a flow velocity of the fluid is measured continuously as a function of a change in the temperature of said heat generating means; and said thermally conductive heat radiating means having said substantially flat portion thereof arranged in close proximity to said outer portion of said heat generating means through the intermediary of said resin layer which surrounds both said heat generating means and said detection means, and wherein an outer surface portion of said resin layer facing toward the fluid is fully covered by said substantially flat portion of said thermally conductive heat radiating means which directly contacts the fluid and said resin layer does not contact the fluid, so that the heat generated by said heat generating means is transmitted to the fluid first through said resin layer and then through said substantially flat portion of said thermally conductive heat radiating means.

2. The flow-velocity sensor probe of claim 1, wherein said thermally conductive heat radiating means comprises a metal member.

3. The flow-velocity sensor probe of claim 2, wherein said metal member comprises gold.

4. The flow-velocity sensor probe of claim 1, wherein said means for increasing the thermal conductivity of said resin layer comprises a resin and a thermally conductive material exhibiting a high thermal conductivity and a high resistivity mixed in said resin.

5. The flow-velocity sensor probe of claim 4, wherein said thermally conductive material comprises at least one member selected from the group consisting of boron nitride, silicon nitride, alumina and diamond.

6. A flow-velocity sensor probe according to claim 1, wherein said thermally conductive heat radiating means comprises a metal ring for transmitting heat generated by said heat generating means to the fluid.

7. A flow-velocity sensor probe according to claim 1, wherein said heat generating means and said detection means together comprise a single self heated thermistor.

8. A flow-velocity sensor probe according to claim 1, wherein said resin layer completely surrounds both said heat generating means and said detection means.

* * * * *

UNITED STATES PATENT AND TRADEMARK OFFICE
CERTIFICATE OF CORRECTION

PATENT NO. : 5,373,850
DATED : December 20, 1994
INVENTOR(S) : KOHNO et al.

It is certified that error appears in the above-indentified patent and that said Letters Patent is hereby corrected as shown below:

Column 8, line 51 (claim 4), delete "layer" and "a resin and"

Signed and Sealed this

Sixteenth Day of July, 1996

Attest:

BRUCE LEHMAN

Attesting Officer     Commissioner of Patents and Trademarks